(12) United States Patent
Koike et al.

(10) Patent No.: US 9,895,129 B2
(45) Date of Patent: Feb. 20, 2018

(54) CT-IMAGE PROCESSING APPARATUS AND METHOD

(71) Applicant: Rigaku Corporation, Tokyo (JP)

(72) Inventors: Takafumi Koike, Tokyo (JP); Minoru Maesawa, Musashimurayama (JP); Yukihiro Hara, Hino (JP)

(73) Assignee: Rigaku Corporation, Tokyo (JP)

( * ) Notice: Subject to any disclaimer, the term of this patent is extended or adjusted under 35 U.S.C. 154(b) by 63 days.

(21) Appl. No.: 15/070,288

(22) Filed: Mar. 15, 2016

(65) Prior Publication Data

US 2016/0287203 A1  Oct. 6, 2016

(30) Foreign Application Priority Data

Mar. 30, 2015  (JP) ................................ 2015-069710

(51) Int. Cl.
*G06K 9/00* (2006.01)
*A61B 6/00* (2006.01)
(Continued)

(52) U.S. Cl.
CPC .......... *A61B 6/5288* (2013.01); *A61B 6/032* (2013.01); *A61B 6/487* (2013.01); *A61B 6/508* (2013.01);
(Continued)

(58) Field of Classification Search
CPC ... A61B 5/0004; A61B 5/0013; A61B 5/0033; A61B 5/0073; A61B 5/027; A61B 5/032; A61B 5/08; A61B 5/0806; A61B 5/0813; A61B 5/082; A61B 5/087; A61B 5/113; A61B 5/0402; A61B 5/4023;
(Continued)

(56) References Cited

U.S. PATENT DOCUMENTS 7,945,305 B2 *  5/2011  Aggarwal ..........  G01R 33/5673
                                                600/407
8,437,524 B2     5/2013  Bontus et al.
(Continued)

FOREIGN PATENT DOCUMENTS

JP   2009-225850 A   10/2009
JP   2010-515477 A    5/2010
JP      5545881 B2    7/2014

*Primary Examiner* — Jose Couso
(74) *Attorney, Agent, or Firm* — Birch, Stewart, Kolasch & Birch, LLP

(57) ABSTRACT

Provided are a CT-image processing apparatus and a method which can remove noise caused by one of a heartbeat and a breathing beat and extract only an accurate periodic motion by the other one. A CT-image processing apparatus 5 that processes projection data in which an animal is captured as a subject at each time by an X-ray CT apparatus includes a breathing beat threshold specification unit 36a to specify a lower limit of a breathing beat frequency from a feature amount waveform within a ROI for breathing beat synchronization in a series of projection data, a heartbeat threshold specification unit 37a to specify a lower limit of a heartbeat frequency from a feature amount waveform within a ROI for heartbeat synchronization in the series of projection data, a breathing beat extraction unit 36b to extract a breathing beat waveform using a band-pass filter defined by the lower limit of the breathing beat frequency and the lower limit of the heartbeat frequency.

14 Claims, 17 Drawing Sheets

(51) Int. Cl.
*G06T 11/00* (2006.01)
*A61B 6/03* (2006.01)

(52) U.S. Cl.
CPC .......... *A61B 6/5217* (2013.01); *G06T 11/005* (2013.01); *A61B 6/503* (2013.01)

(58) Field of Classification Search
CPC ... A61B 5/7207; A61B 5/7285; A61B 5/7289; A61B 6/03–6/032; A61B 6/037; A61B 6/06; A61B 6/466; A61B 6/469; A61B 6/503–6/504; A61B 6/507–6/508; A61B 6/5288; A61B 6/541; A61B 8/13; A61B 2090/3762; A61N 5/10; A61N 5/1048; A61N 5/1049; A61N 5/1064; A61N 2005/1059; A61N 2005/1061; A61N 2005/1062; G06T 7/0012; G06T 7/0016; G06T 11/003; G06T 11/005; G06T 11/008; G06T 2207/10072; G06T 2207/10076; G06T 2207/10081; G06T 2207/10088; G06T 2207/10101; G06T 2207/10104; G06T 2207/10108; G06T 2207/10116; G06T 2207/10124; G06T 2207/30004; G06T 2210/41; G06T 2211/40; G06T 2211/412; G06K 7/1099; G01N 23/046; Y10S 378/901
See application file for complete search history.

(56) References Cited

U.S. PATENT DOCUMENTS

| | | | | |
|---|---|---|---|---|
| 8,600,132 | B2* | 12/2013 | Razifar | A61B 6/032 |
| | | | | 382/128 |
| 8,731,252 | B2 | 5/2014 | Arakita et al. | |
| 8,781,200 | B2 | 7/2014 | Hara et al. | |
| 9,002,442 | B2* | 4/2015 | Harley | A61B 5/0402 |
| | | | | 600/509 |
| 9,013,471 | B2* | 4/2015 | Lauritsch | A61B 6/5264 |
| | | | | 345/419 |
| 9,036,877 | B2* | 5/2015 | Kyal | A61B 5/7225 |
| | | | | 382/107 |
| 9,414,773 | B2* | 8/2016 | Kabus | A61B 6/5264 |
| 2008/0273785 | A1* | 11/2008 | Kesner | A61B 6/527 |
| | | | | 382/131 |
| 2008/0317313 | A1* | 12/2008 | Goddard | A61B 5/721 |
| | | | | 382/131 |
| 2009/0238424 | A1 | 9/2009 | Arakita et al. | |
| 2009/0310825 | A1 | 12/2009 | Bontus et al. | |
| 2012/0237099 | A1 | 9/2012 | Hara et al. | |
| 2012/0294493 | A1* | 11/2012 | Kim | A61B 6/541 |
| | | | | 382/107 |
| 2013/0166011 | A1* | 6/2013 | Strommer | A61B 5/0066 |
| | | | | 623/1.11 |
| 2016/0128664 | A1* | 5/2016 | Manjeshwar | A61B 6/5264 |
| | | | | 378/20 |
| 2016/0310083 | A1* | 10/2016 | Wang | A61B 5/721 |
| 2016/0324500 | A1* | 11/2016 | Fan | A61B 5/7257 |

* cited by examiner

CT-IMAGE PROCESSING APPARATUS AND METHOD

BACKGROUND OF THE INVENTION

Field of the Invention

The present invention relates to a CT-image processing apparatus and a method which process projection data in which an animal is captured as a subject at each time by an X-ray CT apparatus.

Description of the Related Art

X-ray CT imaging is effective for observing an inside of an animal such as a mouse or a rat. However, an animal cannot hold breath during CT imaging according to the instruction of an operator, like a human being. Further, a heart cannot be stopped in biometric imaging. Therefore, the image of an internal organ such as a heart, lungs, and the neighboring lever is blurred by the influence of heartbeat and breath and is not suitable for the accurate observation and test of a region.

To overcome this situation, there are known a method of obtaining a heartbeat signal using an ECG (electrocardiograph) to perform breathing beat synchronization, and a method of imaging a chest part of a small animal with a video-camera and obtaining breathing beat from the vibration of the chest part to perform the breathing beat synchronization. However, each of these methods needs dedicated apparatus or equipment and imposes a burden in the aspects of cost and operation.

A CT-image processing apparatus disclosed in Patent Literature 1 calculates specific information of a ROI for synchronization at each capturing angle so as to track a regio of a target subject to obtain a strong synchronization signal and measures a feature amount expressing a breathing beat or a heartbeat sufficiently well, and thereby enables simple synchronization processing to be performed by using projection data.

PATENT LITERATURE

Patent Literature 1: Japanese Patent No. 5545881
Patent Literature 2: Japanese Patent Laid-Open No. 2009-225850
Patent Literature 3: Japanese Translation of PCT Application No. 2010-515477

In the above method, however, noise remains in the obtained heartbeat or breathing beat, and it is not possible to accurately catch each phase position in a heartbeat waveform or a breathing beat waveform. For example, although it is comparatively easy to reconfigure a CT image in a deflation period or an inflation period of the lungs, it is difficult to obtain a CT image in an intermediate period therebetween. Further, the CT-image processing apparatus disclosed in Patent Literature 1 needs setting and a special calculation for tracking the ROI.

SUMMARY OF THE INVENTION

The present invention has been achieved in view of such a situation, and aims to provide a CT-image processing apparatus and a method which can remove noise caused by one of the heartbeat and the breathing beat and easily extract only an accurate periodic motion by the other one.

(1) For achieving the above object, a CT-image processing apparatus of the present invention is a CT-image processing apparatus that processes projection data in which an animal is captured as a subject at each time by an X-ray CT apparatus, including: a breathing beat threshold specification unit configured to specify a lower limit of a breathing beat frequency from a feature amount waveform within a ROI for breathing beat synchronization in a series of projection data; a heartbeat threshold specification unit configured to specify a lower limit of a heartbeat frequency from a feature amount waveform within a ROI for heartbeat synchronization in the series of projection data; and a breathing beat extraction unit configured to extract a breathing beat waveform using a band-pass filter defined by the lower limit of the breathing beat frequency and the lower limit of the heartbeat frequency. Thereby, it is possible to remove noise caused by a heartbeat to easily extract only an accurate breathing beat. As a result, it is possible to obtain an accurate CT image at a breathing beat phase desired by a user.

(2) The CT-image processing apparatus of the present invention further includes a heartbeat extraction unit configured to extract a heartbeat waveform using a high-pass filter defined by the lower limit of the heartbeat frequency. Thereby, it is possible to remove noise caused by a breathing beat to easily extract only an accurate heartbeat.

(3) In the CT-image processing apparatus of the present invention, the ROI for breathing beat synchronization includes a diaphragm on the projection data. Since the ROI for breathing beat synchronization includes a region of the diaphragm in this manner, it is possible to clearly detect a breathing beat waveform.

(4) In the CT-image processing apparatus of the present invention, the lower limit of the breathing beat frequency is specified by a peak position having the lowest frequency except a DC component in a Fourier transform waveform obtained from the feature amount waveform within the ROI for breathing beat synchronization. Thereby, it is possible to set a lower limit at which noise can be removed appropriately, and to extract only the breathing beat by a band-pass filter based on this lower limit. Here, the lower limit means a cut off frequency.

(5) The CT-image processing apparatus of the present invention further includes a reconfiguration unit configured to reconfigure a CT image using projection data at a certain breathing beat phase specified in the extracted breathing beat waveform. Thereby, it is possible to obtain a CT image at a certain breathing beat phase.

(6) The CT-image processing apparatus of the present invention further includes a reconfiguration unit configured to reconfigure a CT image using projection data at a certain breathing beat phase specified in the extracted breathing beat waveform and also at a certain heartbeat phase specified in the extracted heartbeat waveform. Thereby, it is possible to obtain a CT image at a certain breathing beat phase and heartbeat phase, and to obtain a clear CT image of an inner organ neighboring a heart and a lung.

(7) A CT-image processing apparatus of the present invention CT-image processing apparatus is a CT-image processing apparatus that processes projection data in which an animal is captured as a subject at each time by an X-ray CT apparatus, including: a heartbeat threshold specification unit configured to specify a lower limit of a heartbeat frequency from a feature amount waveform within a ROI for heartbeat synchronization in a series of projection data; and a heartbeat extraction unit configured to extract a heartbeat waveform using a high-pass filter defined by the lower limit of the heartbeat frequency. Thereby, it is possible to remove noise caused by a breathing beat to easily extract only an accurate heartbeat. As a result, it is possible to obtain an accurate CT image at a heartbeat phase desired by a user.

(8) In the CT-image processing apparatus of the present invention, the ROI for heartbeat synchronization includes a ventricle and a ¼ or more to ⅓ or less range of a heart from an end on a diaphragm side on the projection data. Since the ROI for heartbeat synchronization includes the ventricle and a ¼ or more to ⅓ or less range of a heart on a diaphragm side, it is possible to clearly detect waveforms of the heartbeat and the breathing beat.

(9) In the CT-image processing apparatus of the present invention, the lower limit of the heartbeat frequency is specified by a position of a maximum peak except a DC component peak in a Fourier transform waveform obtained from the feature amount waveform within the ROI for heartbeat synchronization. Thereby, it is possible to set a lower limit at which noise can be removed appropriately, and to extract only the breathing beat or only the heartbeat using a band-pass filter or a high-pass filter based on this lower limit. Here, the lower limit means a cut-off frequency.

(10) The CT-image processing apparatus of the present invention further includes a reconfiguration unit configured to reconfigure a CT image using the projection data at a certain heartbeat phase specified in the extracted heartbeat waveform. Thereby, it is possible to obtain a CT image at a certain heartbeat phase.

(11) In the CT-image processing apparatus of the present invention, the reconfiguration unit reconfigures CT images for at least three different phases in the projection data at the certain breathing beat phase or the certain heartbeat phase. Thereby, for example, it is possible to reconfigure CT images of a lung or a heart in a deflation period, an inflation period, and an intermediate period.

(12) A method of the present invention is a method of causing a computer to process projection data in which an animal is captured as a subject at each time by an X-ray CT apparatus, including the steps of: specifying a lower limit of a breathing beat frequency from a feature amount waveform within a ROI for breathing beat synchronization in a series of projection data; specifying a lower limit of a heartbeat frequency from a feature amount waveform within a ROI for heartbeat synchronization in the series of projection data; and extracting a breathing beat waveform using a band-pass filter defined by the lower limit of the breathing beat frequency and the lower limit of the heartbeat frequency. Thereby, it is possible to remove noise caused by a heartbeat to easily extract only an accurate breathing beat.

(13) A method of the present invention is a method of causing a computer to process projection data in which an animal is captured as a subject at each time by an X-ray CT apparatus, including the steps of: specifying a lower limit of a heartbeat frequency from a feature amount waveform within a ROI for heart best synchronization in a series of projection data; and extracting a heartbeat waveform using a high-pass filter defined by the lower limit of the heartbeat frequency. Thereby, it is possible to remove noise caused by a breathing beat to easily extract only an accurate heartbeat.

According to the present invention, it is possible to remove noise caused by one of a heartbeat and a breathing beat to easily extract only an accurate periodic motion by the other one.

DETAILED DESCRIPTION OF THE INVENTION

Next, embodiments of the present invention will be explained with reference to the drawings. For easy understanding of the explanation, the same reference sign is attached to the same constituent in each of the drawings, and duplicated explanation will be omitted.

(Configuration of an X-Ray CT Apparatus]

Figure 1:
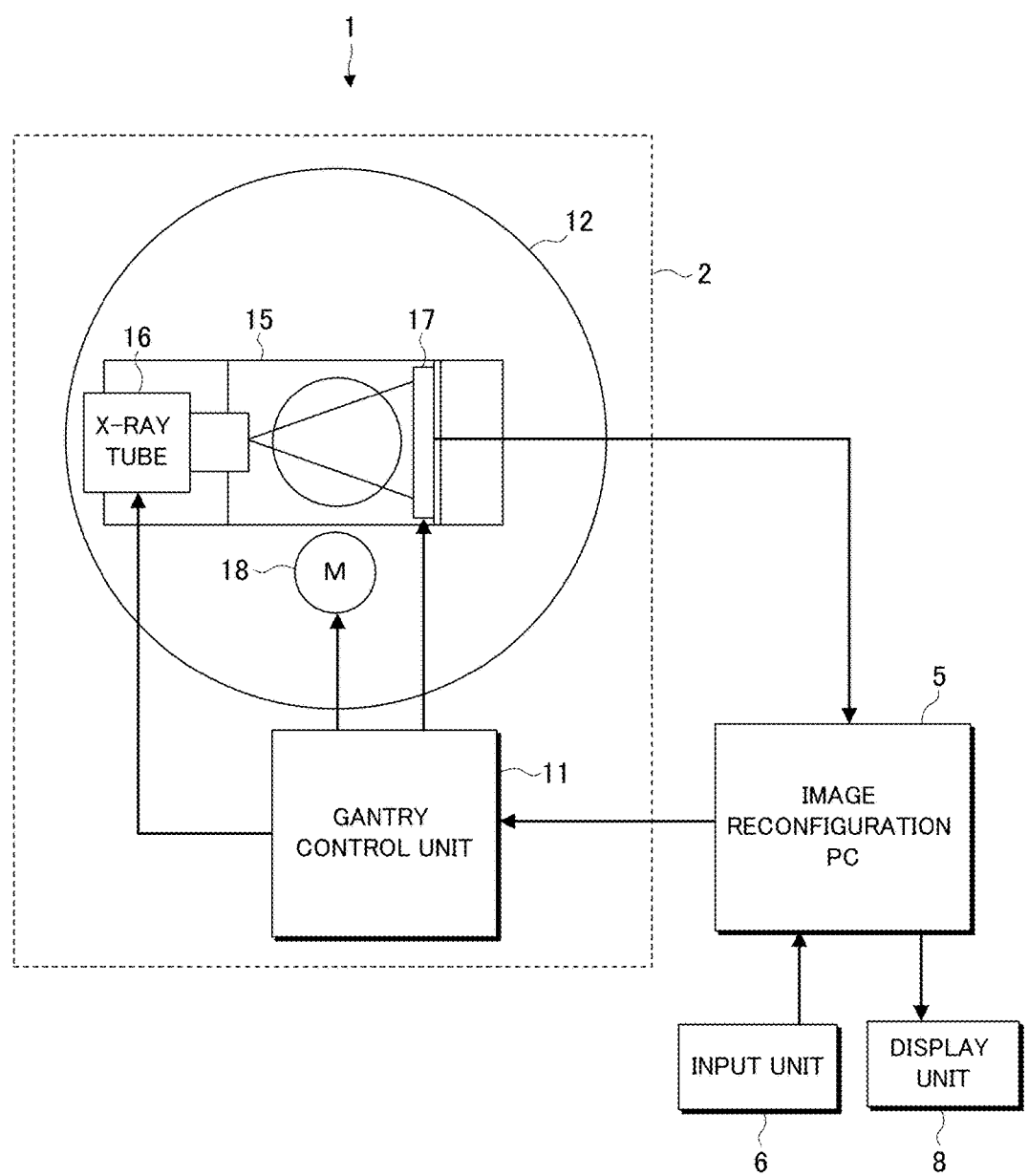
FIG. 1 is a schematic view showing an X-ray CT apparatus of the present invention.

FIG. 1 is a schematic view showing an X-ray CT apparatus 1. As shown in FIG. 1, the X-ray CT apparatus 1 includes a imaging unit 2, an image reconfiguration PC 5 (CT-image processing apparatus), an input unit 6, and a display unit 8. The imaging unit 2 includes a gantry control unit 11 and a gantry 12, and rotates the gantry 12 with respect to a held subject to perform X-ray CT imaging. The imaging unit 2 performs the CT imaging at a calculated timing of CT imaging start, and captures projection data of the subject. The captured CT data is transmitted to the image reconfiguration PC 5. Further, the imaging unit 2 can capture the projection data of a subject. Here, the X-ray CT apparatus 1, while being applicable to a case that a small animal such as a mouse or a rat is set as a subject, is suitable for a case that a medium-size animal such as a monkey or a dog is set as a subject.

The gantry 12 is provided so as to be rotated around the subject for obtaining fluoroscopic data of the subject at a certain rotation angle and for obtaining projection data by rotation imaging. The gantry 12 is provided with a rotation arm 15, an X-ray tube 16, a detector 17, and an arm rotation motor 18. The X-ray tube 16 and the detector 17 are fixed to the rotation arm 15. The rotation arm 15 is disposed within the gantry 12 so as to be rotatable with a point between the X-ray tube 16 and the detector 17 as the center.

The X-ray tube 16 generates an X-ray and irradiates the detector 17. The detector 17 has a reception face to receive the X-ray and is formed like a panel. The X-ray is emitted from the X-ray tube 16 and transmitted through the subject to be detected by the detector 17. The arm rotation motor 18 rotates the rotation arm 15 and thereby rotates the entire gantry 12. The arm rotation motor 18 can rotate the gantry 12 at a set speed in the CT imaging. Further, after the imaging, the arm rotation motor 18 can rotate the gantry 12 in the opposite direction to the original position. Note that, while the X-ray CT apparatus 1 is explained above as an arm type apparatus, an apparatus to which the present invention is applied is not necessarily limited to this type.

The X-ray CT apparatus 1 can collect a large amount of data in a high speed by using a high-speed detector 17 to shorten a imaging time. Further, the X-ray CT apparatus 1 can reduce the influence of a body motion by the high-speed data collection. The frame rate is preferably not lower than 30 fps, and more preferably not lower than 100 fps.

The image reconfiguration PC 5 (CT-image processing apparatus) obtains the captured projection data, and calculates a feature amount as a synchronization signal of a breathing beat or a heartbeat from the projection data. Then, the image reconfiguration PC 5 reconfigures three-dimensional CT image data using the breathing beat or heartbeat synchronization signal. Further, the image reconfiguration PC 5 has also functions of transmitting a imaging condition and the like to the imaging unit 2 and controlling the operation of the imaging unit 2. The input unit 6 such as a keyboard or a mouse receives an input from a user and transmits the input signal to the image reconfiguration PC 5.

The display unit 8 such as a display device displays a fluoroscopic image and the obtained synchronization signal. Further, the display unit 8 displays the projection data during the CT imaging and displays the CT image data after the image reconfiguration. The gantry control unit 11, upon receiving an instruction from the image reconfiguration PC 5, controls the rotation of the gantry 12 at an instructed speed, and controls the CT imaging by the X-ray tube 16 and the detector 17.

(Configuration of an Image Reconfiguration PC)

Figure 2:
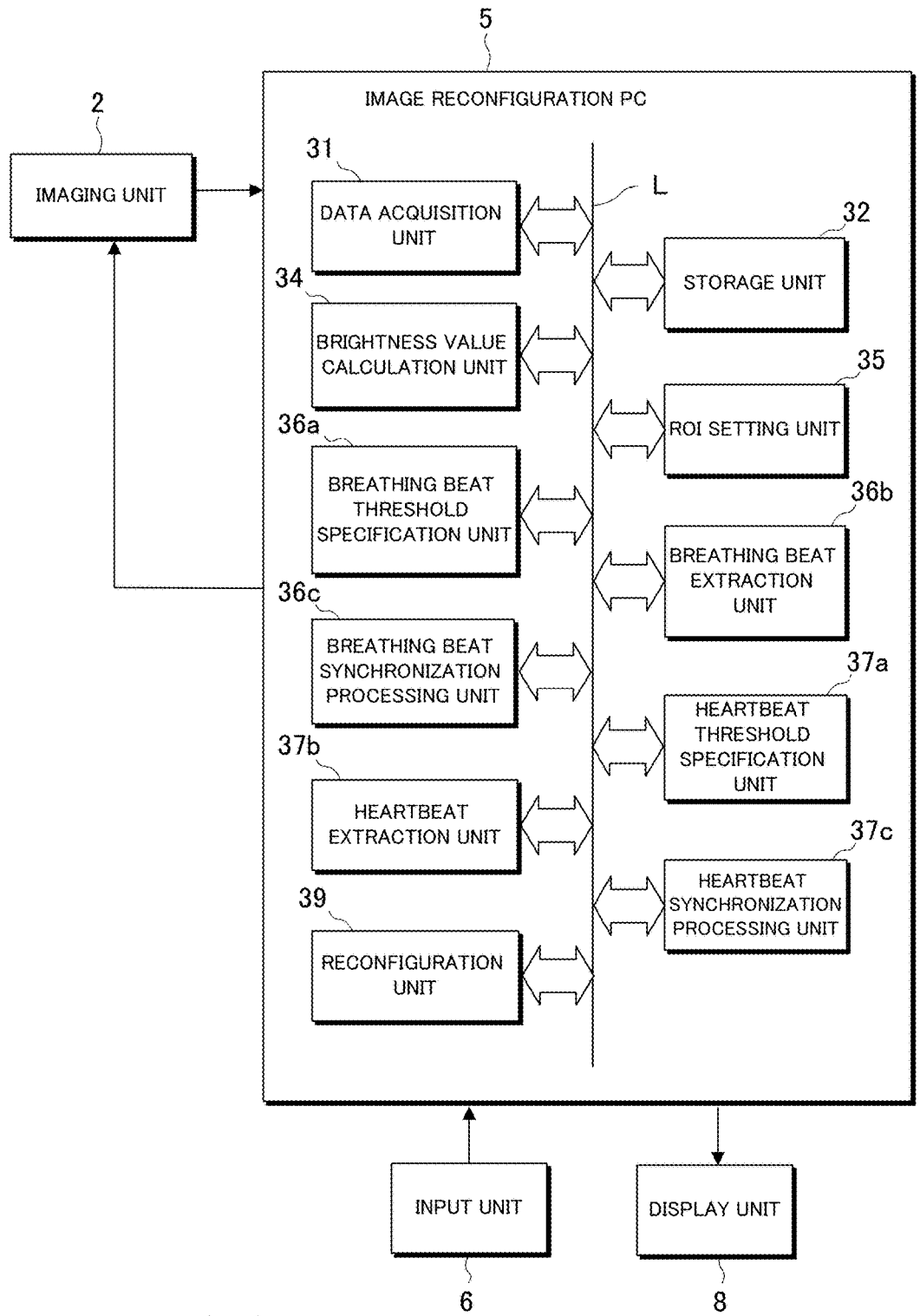
FIG. 2 is a block diagram showing an X-ray CT apparatus of the present invention.

Next, the image processing function will be explained in more detail. FIG. 2 is a block diagram showing the X-ray CT apparatus 1. As shown in FIG. 2, the image reconfiguration PC 5 receives a user input from the input unit 6 such as the keyboard or the mouse. On the other side, the image reconfiguration PC 5 displays the fluoroscopic image and an input screen, and the like on the display unit 8 such as the display device. In the imaging, the image reconfiguration PC 5 transmits the control information input by the user to the imaging unit 2.

Further, the image reconfiguration PC 5 includes a data acquisition unit 31, a storage unit 32, a brightness value calculation unit 34 (feature amount calculation unit), a ROI setting unit 35, a breathing beat threshold specification unit 36a, a breathing beat extraction unit 36b, a breathing beat synchronization processing unit 36c, a heartbeat threshold specification unit 37a, a heartbeat extraction unit 37b, a heartbeat synchronization processing unit 37c, and a reconfiguration unit 39, and extracts a periodic motion of a heart or a lung of a subject to process the projection data. Each of the units can transmit or receive information via a control bus L. Here, the image reconfiguration PC 5 is configured substantially with a CPU, and a memory or a hard disk, and the like.

The data acquisition unit 31 acquires the fluoroscopic data and the projection data of the subject from the imaging unit 2. The storage unit 32 stores the acquired projection data of the subject. Further, the storage unit 32 stores a brightness value calculated by the brightness value calculation unit 34 and the feature amount which is an average value of the brightness values.

The brightness value calculation unit 34 integrates the brightness values across the inside of the ROI (Region of Interest) for synchronization set in the acquired projection data, and divides the integrated value by the number of pixels in the ROI for synchronization. Thereby, an average value of the brightness values (feature amount) is calculated as a breathing beat or heartbeat synchronization signal. Note that the feature amount is not necessarily the brightness value, and may be a value corresponding to an integrated value of a certain region. Here, the calculation of the ROI for synchronization is performed during the data collection or after the collection. Note that the ROI for synchronization is different from a ROI for observation in use, and used for the purpose of catching a clear signal having a periodic motion.

The ROI setting unit 35 causes the ROI for synchronization to be stored in the fluoroscopic observation. It is preferable to confirm that the same setting of the ROI for synchronization can be used for the fluoroscopic data at a plurality of angles without a problem. A ROI for breathing beat synchronization is input from the input unit 6 by the user. The plurality of capturing angles is preferably two capturing angles forming an angle not smaller than 60 degrees and not larger than 120 degrees therebetween, and more preferably two angles crossing each other perpendicularly.

In this manner, each of a heartbeat signal and a breathing beat signal is obtained from the ROI for synchronization of the projection data. Then, the blur of the images caused by the heartbeat or the breathing beat is eliminated and image quality is considerably improved. Then, it is possible to obtain heart synchronized images not only in the inflation period and the deflation period but also in the intermediate phase therebetween, and to utilize the images for a heart function test.

The breathing beat threshold specification unit 36a specifies a lower limit of a breathing beat frequency from a feature amount waveform within the ROI for breathing beat synchronization in a series of projection data. The specification of the lower limit will be described below in detail. The breathing beat extraction unit 36b extracts a breathing beat waveform using a band-pass filter defined by the lower limit of the breathing beat frequency and a lower limit of a heartbeat frequency. Specifically, the breathing beat extraction unit 36b performs processing of causing a frequency between the above both thresholds to pass and cutting off a frequency except the above frequency. Thereby, it is possible to remove noise caused by a heartbeat and to easily extract only an accurate breathing beat.

The breathing beat synchronization processing unit 36c selects each projection data by classifying the projection data into a predetermined phase division using a relationship between the capturing angle and the feature amount of the ROI for synchronization in the breathing beat waveform. The predetermined phase division of the breathing beat is a deflation period, an inflation period, or an intermediate phase therebetween of a lung, for example. The synchronization processing like this does not need special hardware and is performed by only software.

The heartbeat threshold specification unit 37a specifies a lower limit of a heartbeat frequency from a feature amount waveform within a ROI for heartbeat synchronization in the series of projection data. The specification of the lower limit will be described below in detail. The heartbeat extraction unit 37b extracts a heartbeat waveform using a high-pass filter defined by the lower limit of the heartbeat frequency. Thereby, it is possible to remove noise caused by a breathing beat and to easily extract only an accurate heartbeat.

The heartbeat synchronization processing unit 37c selects each projection data by classifying the projection data into a predetermined phase division using a relationship between the capturing angle and the feature amount of the ROI for synchronization in the heartbeat waveform. The predetermined phase division of the heartbeat is a deflation period, an inflation period, or an intermediate phase therebetween of a heart, for example. The synchronization processing like this does not need special hardware and is performed by only software.

The heartbeat synchronization processing unit 37c selects the projection data classified into the predetermined phase division of the breathing beat in the breathing beat synchronization processing unit 36c, by classifying the projection data into a predetermined heartbeat phase division using the relationship between the capturing angle and the feature amount of the ROI for synchronization.

In this manner, it is possible to extract projection data by classifying the projection data into a breathing beat phase division and a heartbeat phase division. For example, it is possible to classify projection data into a division except the inflation period of the lung, and further classify the classified data into the inflation period division of the heartbeat.

As the result of the synchronization processing, the reconfiguration unit 39 reconfigures a three-dimensional CT image data with the projection data classified into a predetermined breathing beat or a heartbeat phase division. Thereby, it is possible to obtain a clear CT reconfiguration image also for a regio moving periodically using the projection data classified into the specific breathing beat and heartbeat phase divisions. The reconfiguration unit 39 extracts necessary projection data from the data which is synchronization-processed and corresponds to one rotation of the gantry, and reconfigures the CT image data.

Note that the reconfiguration unit 39 may reconfigure the CT image from the projection data at a certain breathing beat phase specified in the extracted breathing beat waveform and also at a certain heartbeat phase specified in the extracted heartbeat waveform. Thereby, it is possible to obtain a CT image at a certain breathing beat phase and also heartbeat phase, and to obtain a clear CT image of an inner organ neighboring the heart or the lung.

In the reconfiguration processing, it is preferable to interpolate the projection data lost due to classification of the projection data with the projection data near the capturing angle to reconfigure the CT image data. Thereby, it is possible to obtain the clear CT image data efficiently.

(Operating Procedure and Apparatus Operation)

Figure 3:
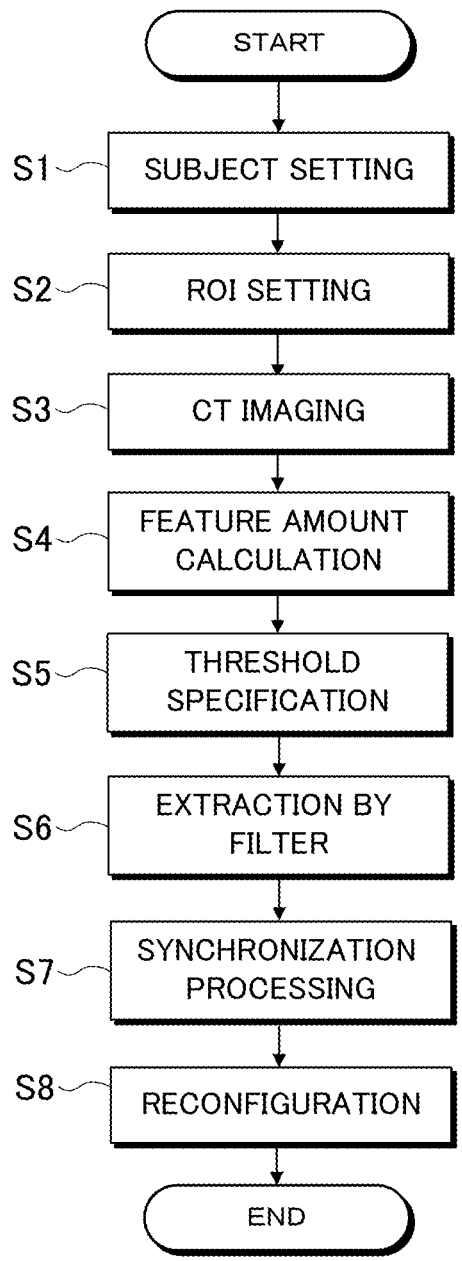
FIG. 3 is a flowchart showing the operation of an X-ray CT apparatus of the present invention.

Next, there will be explained an example of the operating procedure and the apparatus operation of the X-ray CT apparatus 1 configured in this manner. FIG. 3 is a flowchart showing the operation of the X-ray CT apparatus 1.

First, a user sets a subject of a medium-size animal such as a monkey or a dog to a bed provided in the imaging unit 2 (step S1). Then, the subject is irradiated with an X-ray by preliminary imaging and fluoroscopic data is obtained. The preliminary imaging is performed sufficiently for approximately five seconds, and the gantry is not rotated. At this time, real-time processing is performed and each of the breathing beat and heartbeat synchronization signals is calculated and displayed as a graph. The ROI for synchronization is set in a region indicating a regio including a diaphragm or a heart regio in the obtained fluoroscopic data (step S2).

The X-ray CT apparatus 1 receives position and shape information to specify the ROI for synchronization from the user, and thereby manual designation becomes possible. For example, a diagonal line is set by drag-and-drop operation with a mouse, and thereby a rectangular ROI for synchronization can be set. Further, preferably, X-ray irradiation is performed at an angle perpendicular to a capturing angle where the ROI for synchronization is set, and thereby it is confirmed that the ROI for synchronization covers the diaphragm regio and the heart regio in the obtained projection data. Note that the shape of the ROI for synchronization is not necessarily a strict rectangle.

Then, X-ray CT imaging is performed on the subject, and the projection data is acquired (step S3). That is, upon receiving an input of imaging start from the user, the X-ray CT apparatus 1 rotates the gantry to start the imaging, and captures the projection data of the subject in response to a trigger signal.

Then, the X-ray CT apparatus 1 calculates an average value of count values (brightness values) within the ROI for synchronization as the feature amount (step S4). The average value of the count values can be calculated by means of integrating the count values within the ROI and dividing the integrated value by the number of pixels. The waveform of the feature amount for each frame (each angle or time) obtained in each ROI in this manner is Fourier-transformed, and the lower limit is specified for each of the breathing beat extraction and the heartbeat extraction from the feature of the obtained waveform (step S5). Details of the lower limit specification will be described below.

Next, only the breathing beat waveform is extracted by the band-pass filter and only the heartbeat waveform is extracted by the high-pass filter based on the obtained lower limits (step S6). Upon receiving an instruction from the user, the X-ray CT apparatus 1 specifies the projection data classified into the intermediate phase of the lung designated by the breathing beat synchronization as the synchronization processing, for reconfiguration of the three-dimensional CT image data, when receiving an instruction demanding an image of the lung at an intermediate phase between the deflation period and the inflation period (step S7), and reconfigures the three-dimensional CT image data with the specified projection data (step S8) and terminates the processing.

Note that, while an example of the synchronization processing using the breathing beat is explained in the above, in the case of the heartbeat synchronization, the X-ray CT apparatus 1 can specify the projection data in the deflation period, the inflation period, or the intermediate phase therebetween of the heart for the reconfiguration of three-dimensional CT image data utilizing the heartbeat waveform extracted in steps S6 to S8, and can reconfigure the three-dimensional CT image data with the specified projection data. While the entire operation is explained above, subsequently, each specific process will be explained.

(Setting of the ROI for Synchronization)

Figure 4:
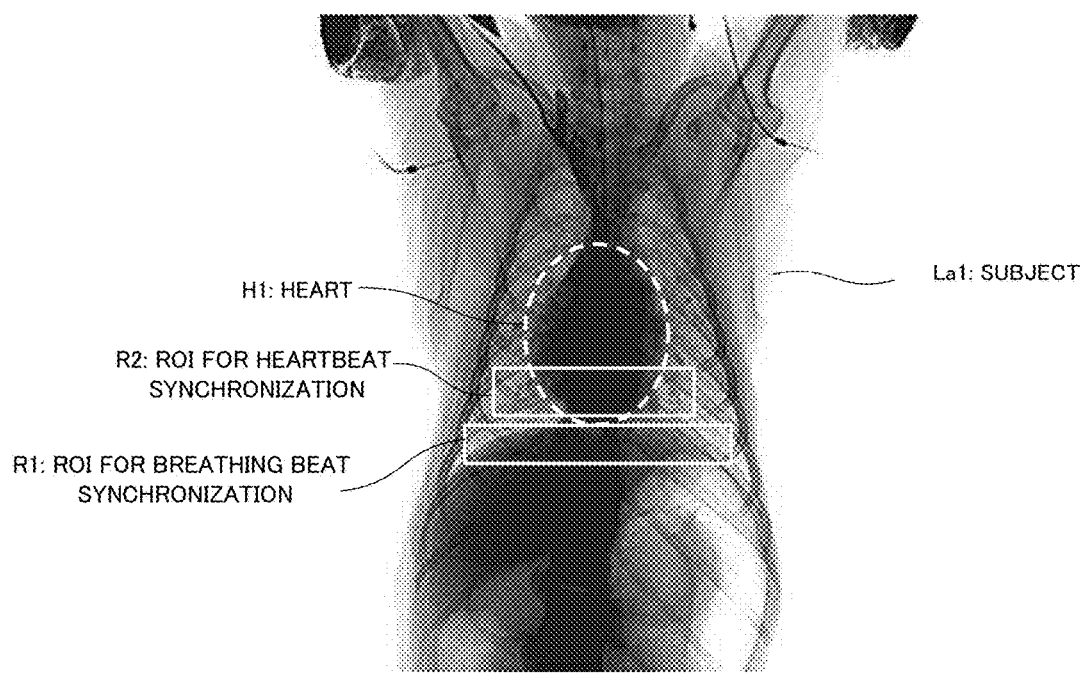
FIG. 4 is a diagram showing a ROI setting screen.

A setting method of the ROI for synchronization will be specifically explained. FIG. 4 is a diagram showing a ROI setting screen. The portion indicated by a black circle at the center of the screen shown in FIG. 4 is a region H1 indicating a heart regio, and a region indicating a diaphragm regio exists directly thereunder (position contacting the heart on the tail side). The user can easily specify this position.

It is preferable to set the ROI for breathing beat synchronization (R1) in a region including the diaphragm regio. Thereby, it is possible to detect the breathing beat waveform clearly. The ROI for heartbeat synchronization (R2) is set preferably so as to include a ventricle and also a ¼ or more to ⅓ or less range of a heart from the end on a diaphragm side on the projection data. Note that the ROI for heartbeat synchronization (R2) may be set so as to cover only an atrium.

Preferably, the ROI for breathing beat synchronization (R1) is set manually, and the ROI for heartbeat synchronization (R2) is set automatically. Further, the ROI for synchronization, while being able to have a desired size in the direction perpendicular to the body axis, preferably has a size not smaller than the size of a target inner organ regio in the direction perpendicular to the body axis. Further, for reducing noise, the ROI for synchronization, while preferably having a width not larger than the body width of the subject, may have a width size across the whole screen. Note that, while the two kinds of ROI for synchronization are set in the above example, more than two kinds of ROI for synchronization may be set.

(Extraction of the Heartbeat Waveform)

Figure 5:
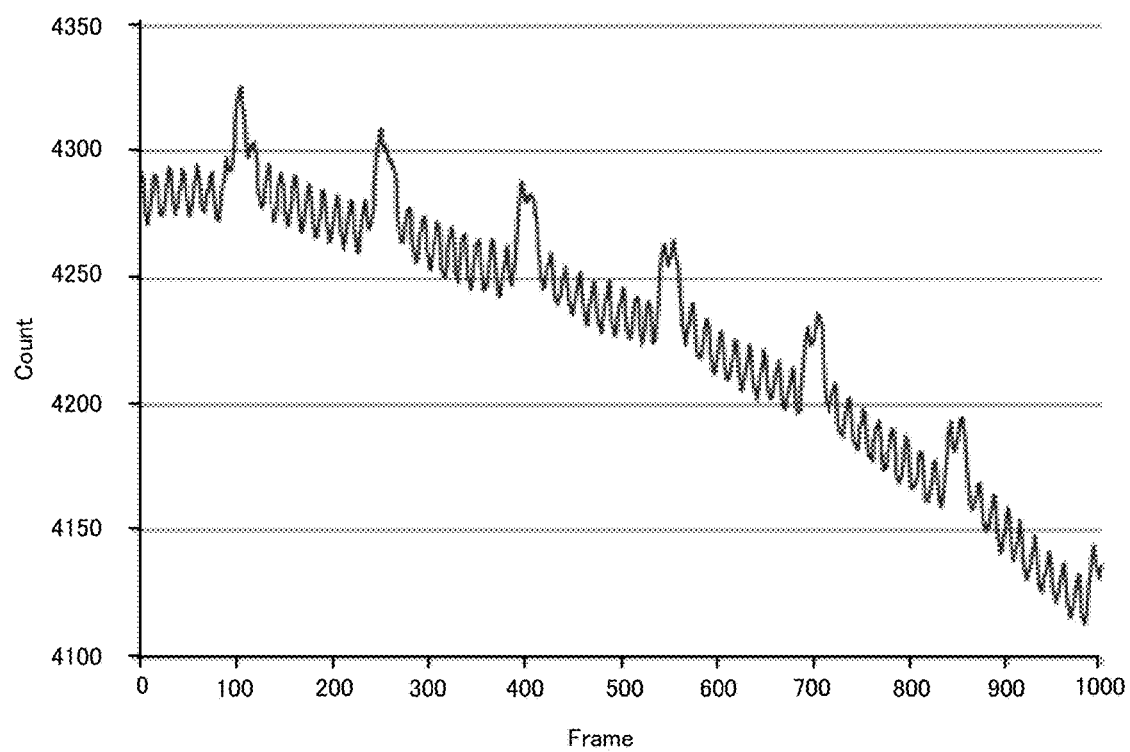
FIG. 5 is a graph showing a feature amount waveform within a ROI for heartbeat synchronization.

Next, a series of processing to extract the heartbeat waveform will be explained specifically. FIG. 5 is a graph showing a feature amount waveform within the ROI for heartbeat synchronization. The feature amount waveform within the ROI for heartbeat synchronization is obtained by means of integrating the brightness values across the inside of the ROI for heartbeat synchronization, dividing the integrated value by the number of pixels in the ROI for synchronization, and plotting the divided value along the number of frames. The horizontal axis of the graph expresses the number of frames, and the number of frames is equivalent to time. The vertical axis of the graph expresses a count as the feature amount. The waveform shows a long period (DC component) peak, a short period peak (breathing beat component), and a further short period peak (heartbeat component).

Figure 6:
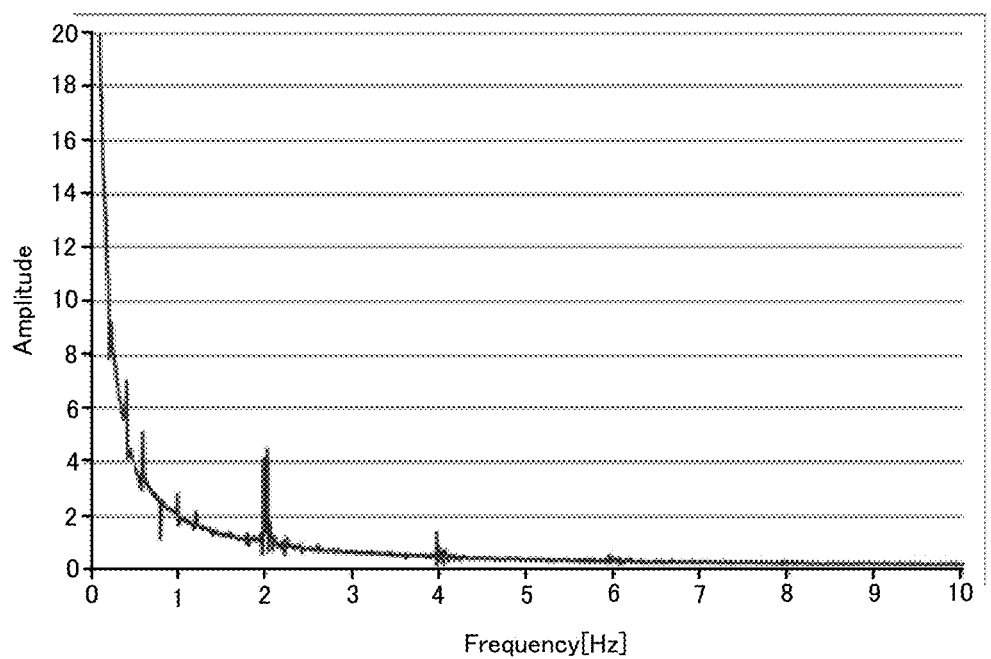
FIG. 6 is a graph obtained by Fourier-transforming a feature amount waveform.

FIG. 6 is a graph obtained by Fourier-transforming the feature amount waveform. In FIG. 6, the position of the maximum peak except 0 Hz (DC component) peak is 2 Hz. Accordingly, the lower limit for extracting the heartbeat waveform can be set to 2 Hz. Here, the lower limit means a cut-off frequency.

Figure 7:
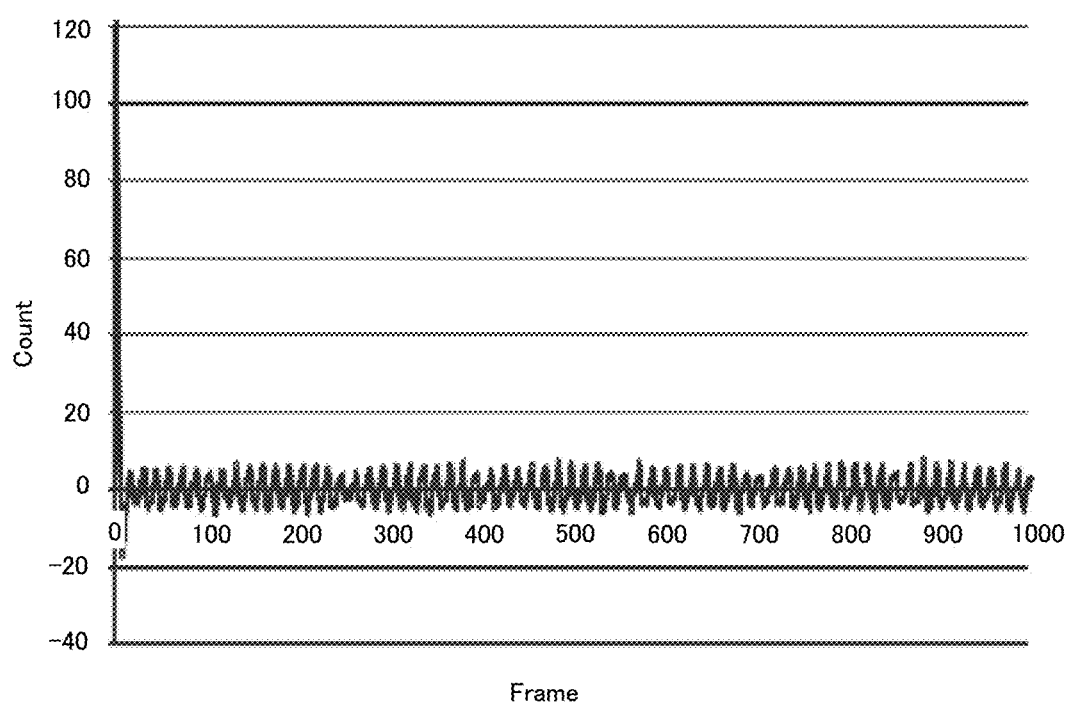
FIG. 7 is a graph showing an extracted heartbeat waveform.

By the use of the high-pass filter defined by the lower limit obtained in this manner, the heartbeat waveform obtained from the feature amount waveform is extracted. Specifically, in the graph of FIG. 6, a frequency component lower than 2 Hz is cut off, and only a frequency component not lower than 2 Hz is inversely Fourier-transformed. FIG. 7 is a graph showing an extracted heartbeat waveform. As the result of the high-pass filter application as above, except for a peak near frame number 0, only beats having approximately the same period and approximately the same amplitude are extracted as the heartbeat waveform.

(Extraction of the Breathing Beat Waveform)

Figure 8:
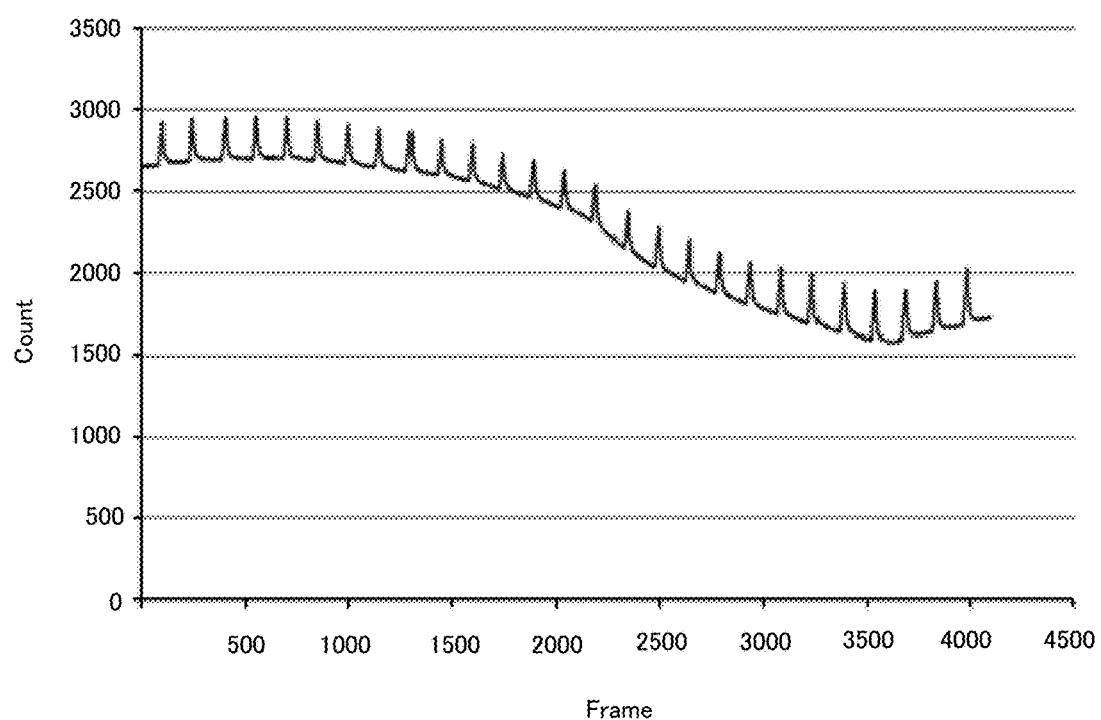
FIG. 8 is a graph showing a feature amount waveform within a ROI for breathing beat synchronization.

Next, a series of processing to extract the breathing beat waveform will be explained specifically. FIG. 8 is a graph showing a feature amount waveform within the ROI for breathing beat synchronization. The feature amount waveform within the ROI for breathing beat synchronization is obtained by means of integrating the brightness values across the inside of the ROI for breathing beat synchronization, dividing the integrated value by the number of pixels in the ROI for synchronization, and plotting the divided value along the number of frames. The horizontal axis of the graph expresses the number of frames. The vertical axis of the graph expresses a count as the feature amount. The waveform shows a long period (DC component) peak, and a short period peak.

Figure 9:
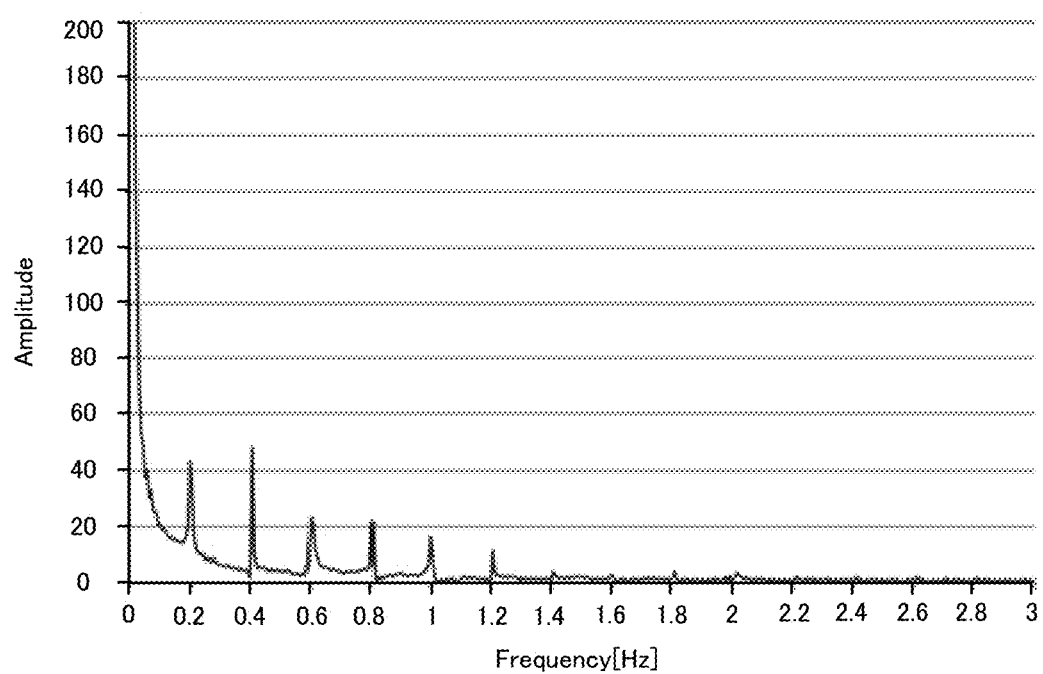
FIG. 9 is a graph obtained by Fourier-transforming a feature amount waveform.

FIG. 9 is a graph obtained by Fourier-transforming the feature amount waveform. In FIG. 9, the position of a peak having the smallest frequency except a 0 Hz peak (DC component) is 0.2 Hz. Accordingly, the lower limit for extracting the breathing beat waveform can be set to 0.2 Hz.

Figure 10:
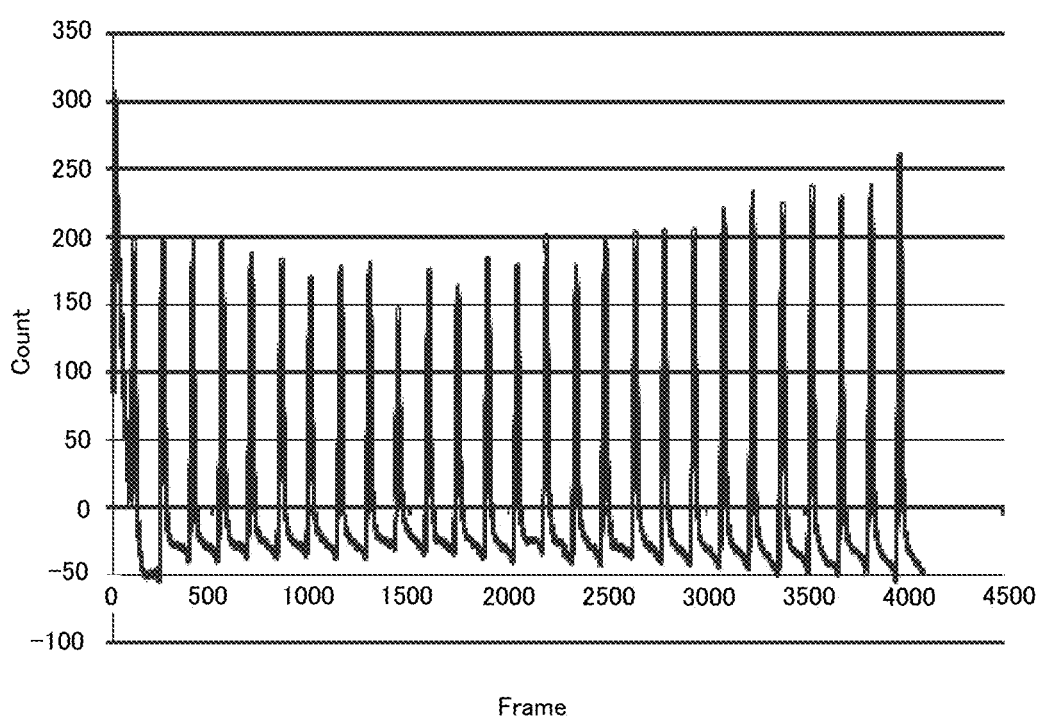
FIG. 10 is a graph showing an extracted breathing beat waveform.

By the use of the band-pass filter defined by the above obtained lower limit for extracting the heartbeat waveform and lower limit for extracting the breathing beat waveform, the breathing beat waveform is extracted from the feature amount waveform. Specifically, in the graph of FIG. 9, a frequency component lower than 0.2 Hz and a frequency component higher than 2 Hz are cut off, and only a frequency component in the band of 0.2 Hz to 2 Hz is inversely Fourier-transformed. FIG. 10 is a graph showing an extracted breathing beat waveform. As the result of the band-pass filter application as above, except for a peak near frame number 0, only beats having approximately the same period and approximately the same amplitude are extracted as the breathing beat waveform.

(Synchronization Processing)

Figure 11:
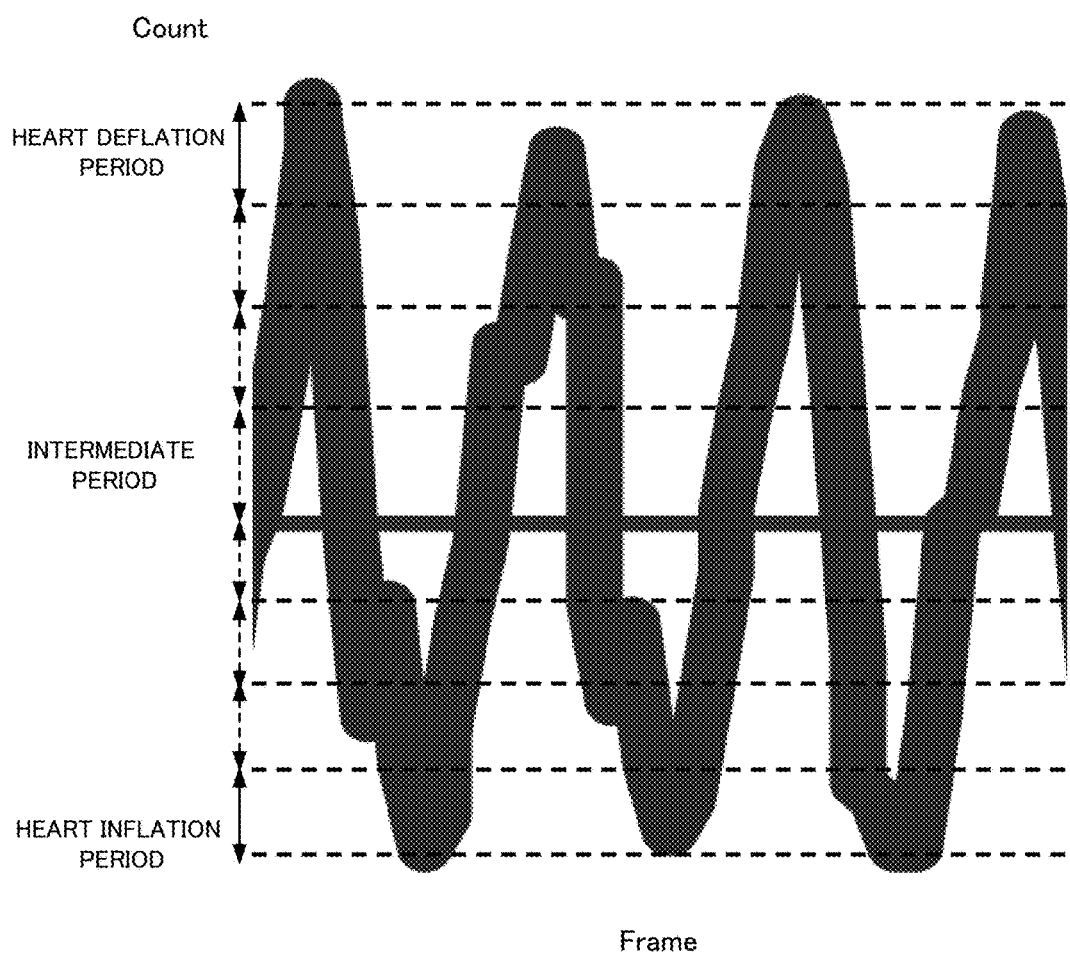
FIG. 11 is a graph showing each phase in an extracted heartbeat waveform.

Next, the synchronization processing will be specifically explained. When the waveform extracted as above is divided into predetermined count bands, a frame in an interval corresponding to the count band can be treated as the projection data of the phase. FIG. 11 is a graph showing each phase of the extracted heartbeat waveform. For example, the projection data corresponding to a phase section of the heart deflation period is obtained by the selection of a frame included in a band of the largest feature amount among ¼ amplitude bands in the graph shown in FIG. 11. Further, the projection data corresponding to a phase section as the heart inflation period is obtained by the selection of a frame included in a band of the smallest feature amount among the ¼ amplitude bands in the graph shown in FIG. 11.

Further, as shown in FIG. 11, one of the six sections is selected as the intermediate period between the heart deflation period and the heart inflation period, and the projection data can be also selected so as to be included in the phase section. Here, when the waveform amplitude is expressed by A, the frame rate is expressed by fs, and the heartbeat frequency is expressed by fc, the period of each phase can be calculated by 4·A·fc/fs. In this manner, it is possible to perform the synchronization processing in a desired phase interval among the many phase intervals. Note that, while the frame in each of the deflation period, the inflation period, or the intermediate period of the heart is selected in the extracted heartbeat waveform for the synchronization processing in the above example, a frame in the deflation period, the inflation period, or the intermediate period of the lung can be selected similarly in the extracted breathing waveform for the synchronization processing.

(CT Reconfiguration)

Figure 12:
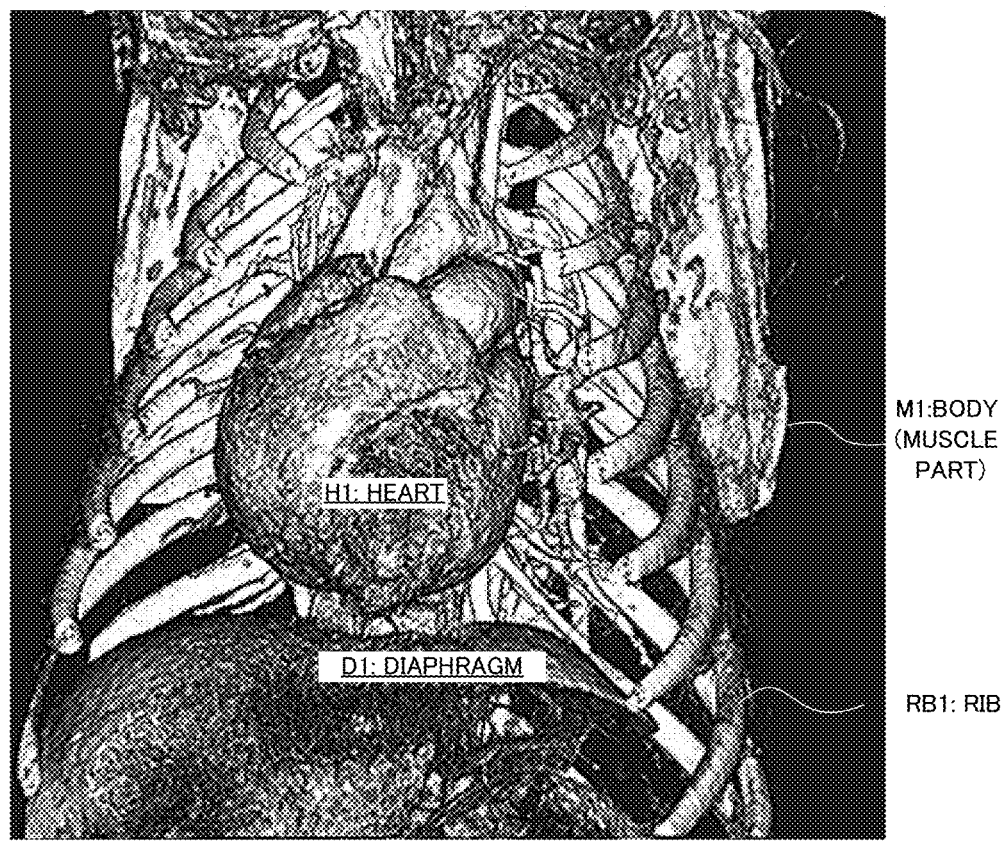
FIG. 12 is a three-dimensional CT image reconfigured with projection data of a heart in a deflation period.
Figure 13:
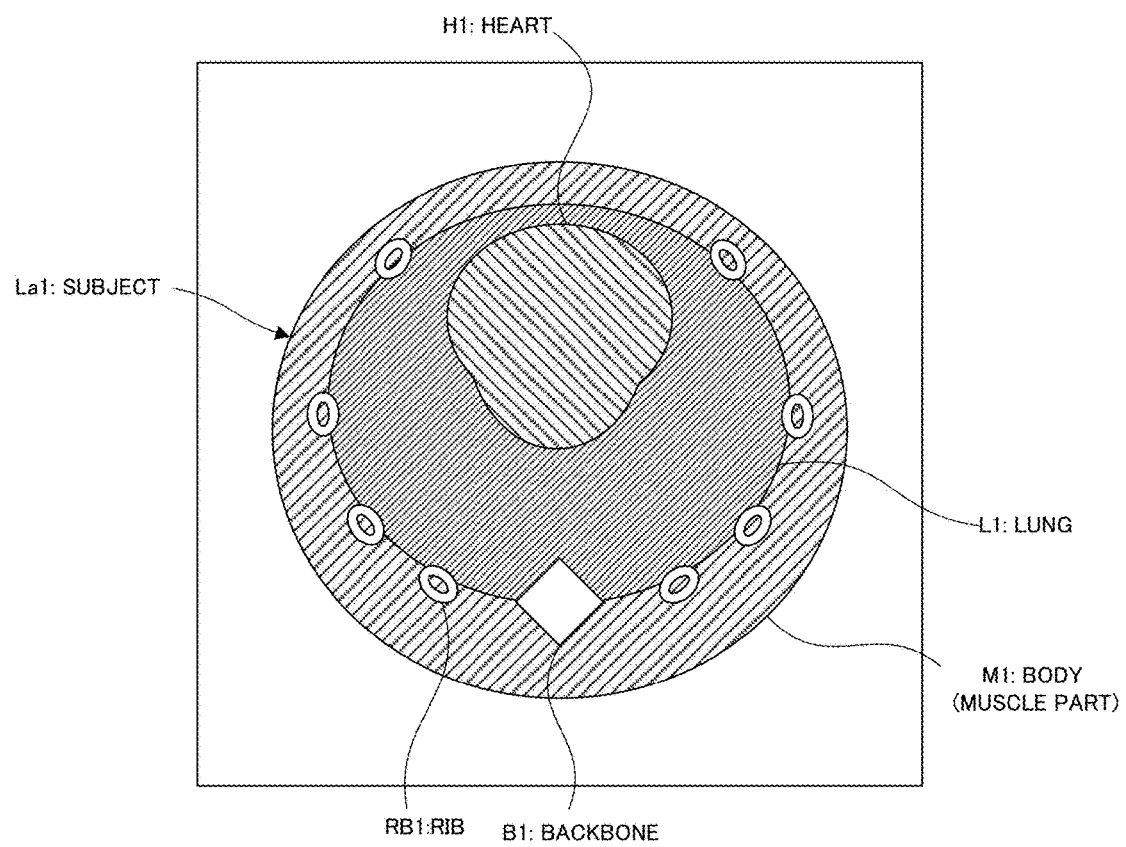
FIG. 13 is a schematic view showing a CT cross-sectional view of a heart in an inflation period.
Figure 14:
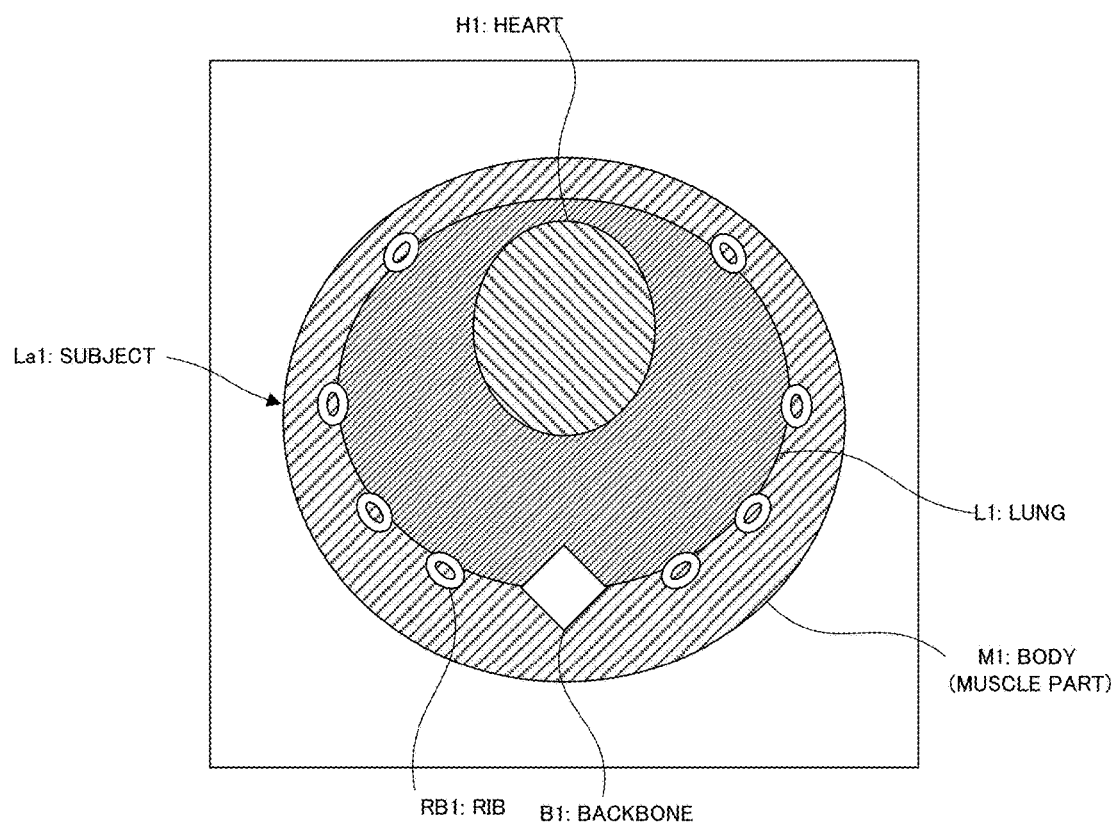
FIG. 14 is a schematic diagram showing a CT cross-sectional view of a heart in a deflation period.

As above, it is possible to extract the projection data at a certain phase in the heartbeat waveform or the breathing beat waveform and to configure the three-dimensional CT image. In this case, it is also possible to further obtain a CT cross-sectional image from the obtained three-dimensional CT image. FIG. 12 is a three-dimensional CT image reconfigured with the projection data of the heart in the inflation period. FIG. 13 is a schematic diagram showing a CT cross-sectional image of the heart in the inflation period. FIG. 14 is a schematic diagram showing a CT cross-sectional image of the heart in the deflation period.

In FIG. 13 and FIG. 14, the subject La1 is displayed in a cross section perpendicular to the body axis in the three-dimensional CT image. As shown in the drawings, the body (muscle part) M1 exists inside the body surface, and the lungs L1 exist thereinside. Then, it is found that the backbone B1 and the ribs RB1 exist on the boundary thereof, and the heart H1 exists at the center covered by the lungs L1. Further, the diaphragm D1 exists on the tail side of the heart H1, and the periodic motion by the breathing beat appears most notably in the diaphragm D1. Among these internal organs, the heart H1 beats and, therefore, when the synchronization processing is not performed on the heartbeat waveform, the image thereof is blurred. When the synchronization processing is performed as above, however, the heart H1 is displayed clearly in an inflated state in FIG. 13 which shows the case of the inflation period, and displayed clearly in a deflated state in FIG. 12 and FIG. 14 which show the case of the deflation period.

(Verification of the ROI Setting)

Figure 15:
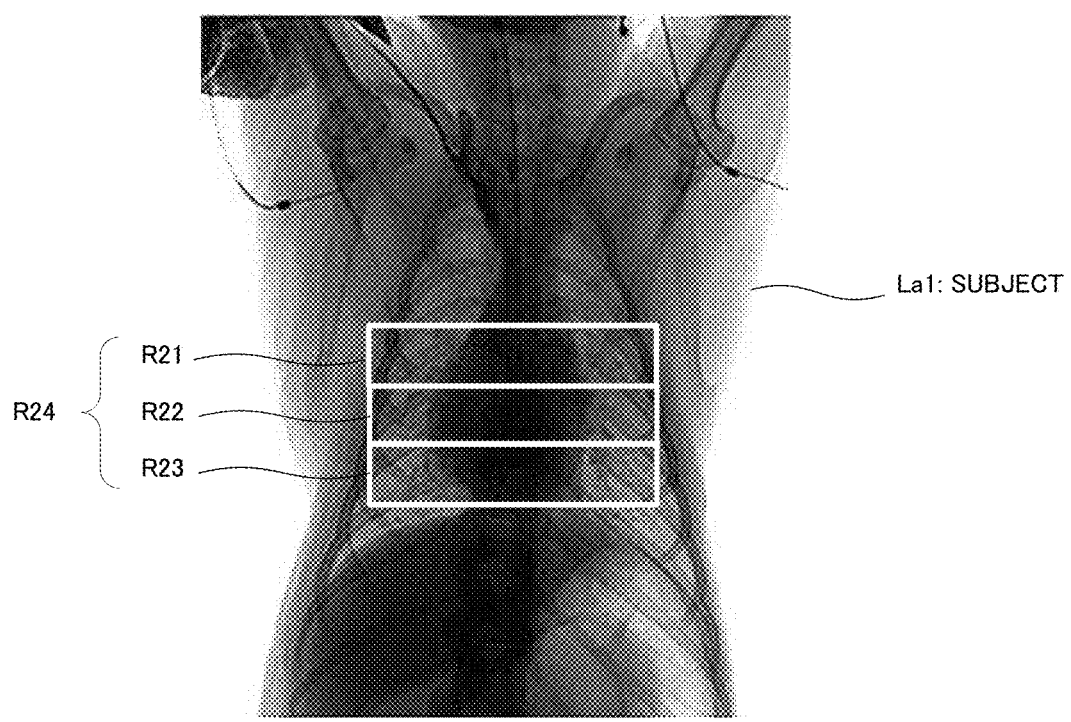
FIG. 15 is a diagram showing a set position of each ROI.

While the ROI for breathing beat synchronization may be set so as to include the diaphragm, for the ROI for heartbeat synchronization, there is a position suitable for the ROI setting even within the heart. FIG. 15 is a diagram showing each of ROI setting positions. As shown in FIG. 15, rectangular ROIs (R21, R22, R23, and R24) are set for the upper (head side) ⅓ part, the center ⅓ part, the lower (diaphragm side) ⅓ part, and the whole part of the heart, respectively, and respective feature amount waveforms are calculated.

Figure 16:
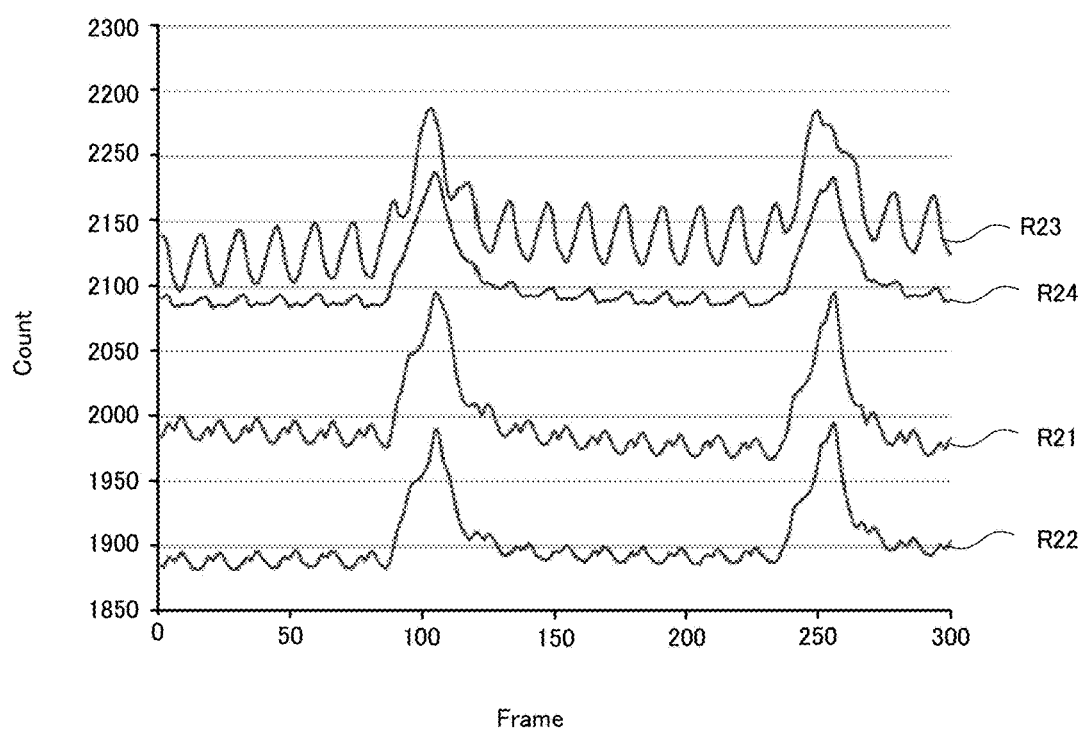
FIG. 16 is a graph showing a waveform of an integrated value of brightness for each ROI set position.

FIG. 16 is a graph showing the feature amount waveform for each of the ROI setting positions. As shown in FIG. 16, it is found that the heartbeat waveform appears most clearly in the graph of the ROI (R23) set for the ⅓ part on the diaphragm side. The atriums are included in the ⅓ to ¼ part of the heart regio on the diaphragm side, and therefore the clear heartbeat waveform could be obtained. Accordingly, it is found that the ROI for heartbeat synchronization is disposed preferably so as to include a ¼ or more to ⅓ or less range of the heart from the end on the diaphragm side.

(Comparison Between the ECG and the Feature Amount Waveform)

Figure 17:
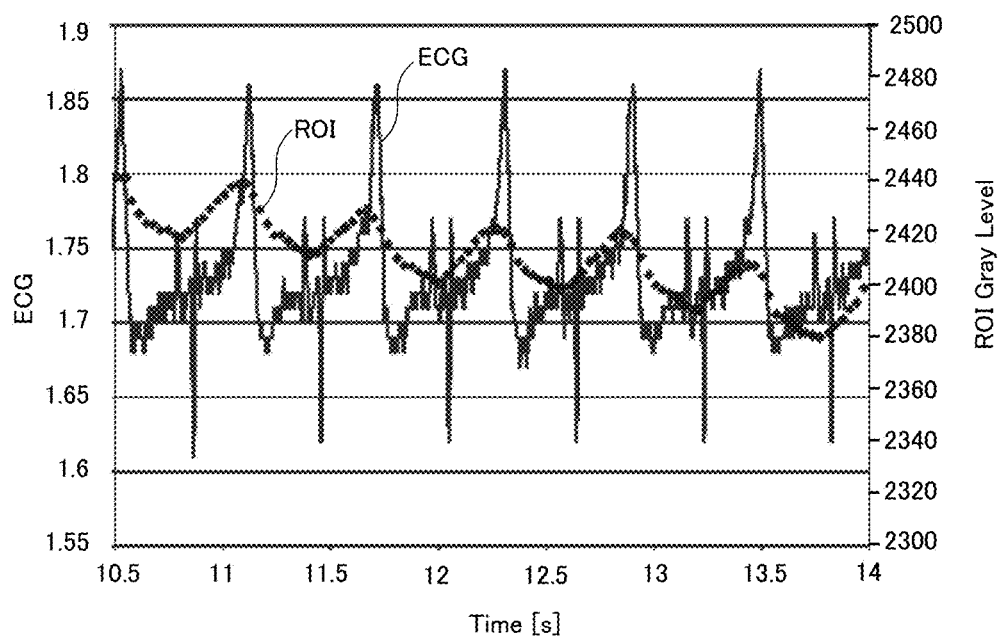
FIG. 17 is a graph showing a comparison between an ECG waveform and an extracted heartbeat waveform.

Next, an electrocardiogram is obtained by the ECG and also the heartbeat waveform is extracted by the calculation of the feature amount within the ROI for heartbeat synchronization in the X-ray CT apparatus 1, for the same subject, and both results are expressed on the same time axis. FIG. 17 is a graph showing a comparison between the ECG waveform and the extracted heartbeat waveform. As shown in FIG. 17, it is confirmed that the peak of the ECG waveform and the peak of the extracted heartbeat waveform coincide with each other.

What is claimed is:

1. A CT-image processing apparatus that processes projection data in which an animal is captured as a subject at each time by an X-ray CT apparatus, comprising:
   a processor; and
   a memory having stored thereon instructions which when read by the processor configure the processor to
      specify a lower limit of a breathing beat frequency from a feature amount waveform within a ROI for breathing beat synchronization in a series of projection data received from an X-ray CT imaging device;
      specify a lower limit of a heartbeat frequency from a feature amount waveform within a ROI for heartbeat synchronization in the series of projection data;
      extract a breathing beat waveform using a band-pass filter defined by the lower limit of the breathing beat frequency and the lower limit of the heartbeat frequency, and
      reconfigure a CT image using projection data at a certain breathing beat phase specified in the extracted breathing beat waveform.

2. The CT-image processing apparatus according to claim 1, wherein the processor is further configured to extract a heartbeat waveform using a high-pass filter defined by the lower limit of the heartbeat frequency.

3. The CT-image processing apparatus according to claim 1, wherein the ROI for breathing beat synchronization includes a diaphragm on the projection data.

4. The CT-image processing apparatus according to claim 1, wherein the lower limit of the breathing beat frequency is specified by a peak position having the lowest frequency except a DC component in a Fourier transform waveform obtained from the feature amount waveform within the ROI for breathing beat synchronization.

5. The CT-image processing apparatus according to claim 2, wherein the processor is further configured to reconfigure the CT image using projection data at a certain breathing beat phase specified in the extracted breathing beat waveform and also at a certain heartbeat phase specified in the extracted heartbeat waveform.

6. A CT-image processing apparatus that processes projection data in which an animal is captured as a subject at each time by an X-ray CT apparatus, comprising:
   a processor; and
   a memory having stored thereon instructions which when read by the processor configure the processor to
      specify a lower limit of a heartbeat frequency from a feature amount waveform within a ROI for heartbeat synchronization in a series of projection data; and
      extract a heartbeat waveform using a high-pass filter defined by the lower limit of the heartbeat frequency; and
      reconfigure a CT image using the projection data at a certain heartbeat phase specified in the extracted heartbeat waveform.

7. The CT-image processing apparatus according to claim 1, wherein the ROI for heartbeat synchronization includes a ventricle and a ¼ or more to ⅓ or less range of a heart from an end on a diaphragm side on the projection data.

8. The CT-image processing apparatus according to claim 6, wherein the ROI for heartbeat synchronization includes a ventricle and a ¼ or more to ⅓ or less range of a heart from an end on a diaphragm side on the projection data.

9. The CT-image processing apparatus according to claim 1, wherein the lower limit of the heartbeat frequency is specified by a position of a maximum peak except a DC component peak in a Fourier transform waveform obtained from the feature amount waveform within the ROI for heartbeat synchronization.

10. The CT-image processing apparatus according to claim 6, wherein the lower limit of the heartbeat frequency is specified by a position of a maximum peak except a DC component peak in a Fourier transform waveform obtained from the feature amount waveform within the ROI for heartbeat synchronization.

11. The CT-image processing apparatus according to claim 1, wherein the processor reconfigures CT images for at least three different phases in the projection data at the certain breathing beat phase or the certain heartbeat phase.

12. The CT-image processing apparatus according to claim 6, wherein the processor reconfigures CT images for at least three different phases in the projection data at the certain breathing beat phase or the certain heartbeat phase.

13. A method of causing a computer to process projection data in which an animal is captured as a subject at each time by an X-ray CT apparatus, comprising the steps of:
- specifying, using a processor, a lower limit of a breathing beat frequency from a feature amount waveform within a ROI for breathing beat synchronization in a series of projection data;
- specifying, u processor, a lower limit of a heartbeat frequency from a feature amount waveform within a ROI for heartbeat synchronization in the series of projection data;
- extracting, using the processor, a breathing beat waveform using a band-pass filter defined by the lower limit of the breathing beat frequency and the lower limit of the heartbeat frequency; and,
- reconfiguring a CT image using projection data at a certain breathing beat phase specified in the extracted breathing beat waveform.

14. The method according to claim 13 further comprising a step of:
- extracting, using the processor, a heartbeat waveform using a high-pass filter defined by the lower limit of the heartbeat frequency.

* * * * *